United States Patent [19]

Oosterwijk

[11] 4,016,187
[45] Apr. 5, 1977

[54] PHENOXY PERACETIC ACID ESTERS

[75] Inventor: Hendrik Harm Jannes Oosterwijk, Diepenveen, Netherlands

[73] Assignee: Akzona Incorporated, Asheville, N.C.

[22] Filed: June 30, 1975

[21] Appl. No.: 592,080

[30] Foreign Application Priority Data

July 5, 1974 Netherlands .................. 7409110

[52] U.S. Cl. .................. 260/453 RZ; 260/861; 260/899; 526/209; 526/216; 526/344
[51] Int. Cl.² .................................. C07C 179/18
[58] Field of Search ........................... 260/453 RZ

[56] References Cited
FOREIGN PATENTS OR APPLICATIONS 661,010  12/1965  Netherlands .................. 260/453

OTHER PUBLICATIONS

Chem. Abst. vol. 64, (1966) pp. 17486c.

Primary Examiner—Lewis Gotts
Assistant Examiner—D. R. Phillips
Attorney, Agent, or Firm—Stevens, Davis, Miller & Mosher

[57] ABSTRACT

Novel peresters having the formula

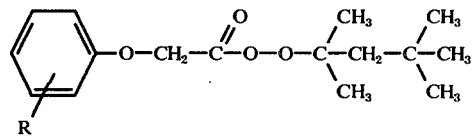

wherein R is hydrogen or an alkyl group or an alkoxy group having 1–6 C atoms and a method for making them are provided. The novel peresters may be used to advantage in the polymerization or copolymerization of ethylenically unsaturated compounds.

4 Claims, No Drawings

PHENOXY PERACETIC ACID ESTERS

This invention relates to novel peresters, to the preparation of these peresters, and to the use thereof as initiators for chemical reactions, more particularly as initiators for the polymerization of vinyl chloride, the copolymerization of vinyl chloride and monomers copolymerizable therewith, and for the copolymerization of unsaturated polyester resins.

It is known that ethylenically unsaturated monomers such as styrene, methyl methacrylate, vinyl chloride, vinylidene chloride, vinyl acetate and other vinyl esters or mixtures of these compounds, such as mixtures of styrene and acrylonitrile, vinyl chloride and vinyl acetate can be polymerized or copolymerized under the influence of organic peroxides yielding free radicals.

When this polymerization or copolymerization is carried out at a low temperature, e.g. between 30° and 60° C., the initiator must be a peroxide which is sufficiently reactive at that temperature.

Polymerization at such a low temperature is particularly desirable in the mass polymerization or the suspension polymerization of vinyl chloride. However, such a polymerization of vinyl chloride carried out using the peroxide which has been known to be the most suitable for this purpose, viz. acetylocyclohexane sulphonyl peroxide, results in the production of a low-porous polyvinyl chloride, which is reflected in the occurrence of fisheyes and in poor heat stability. Moreover, the polymer obtained has a poor absorptivity of softeners.

It has now been found that it is possible to obtain a thermostable polyvinyl chloride polymer having a few fisheyes and a reasonable rate of absorptivity for softeners by polymerizing vinyl chloride or copolymerizing vinyl chloride and monomers copolymerizable therewith in suspension or in mass in the presence of a perester which has been unknown so far and has the following general formula

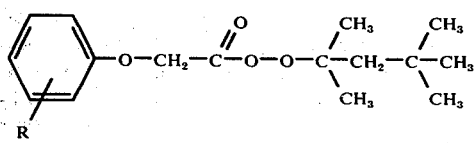

where R represents hydrogen or an alkyl group or alkoxy group with 1–6 C atoms. The polymerization or copolymerization may be carried out at any suitable temperature. The reactivity of the perester is such that the polymerization or copolymerization may be conducted at a low temperature of say about 30° to 60° C. The preferred temperature range is about 40° C to about 60° C.

Any perester of the above formula may be used such as, for example, 2,4,4-trimethyl-2-peroxy phenoxyacetate, 2,4,4-trimethyl pentyl-2-peroxy-4-methyl phenoxyacetate, 2,4,4-trimethyl pentyl-2-peroxy-4-tert.butyl phenoxyacetate and 2,4,4-trimethyl pentyl-2-peroxy-4-methoxy phenoxyacetate.

Any initiating amount of the perester may be used and is contemplated in polymerizing vinyl chloride or in copolymerizing a mixture of vinyl chloride and a monomer copolymerizable therewith, such as, for example, vinylidene chloride, ethylene, propylene, vinyl acetate or the like. Usually the amount of perester will be from about 0.01 to 10% by weight, and preferably about 0.01 to 1% by weight, calculated on the weight of the monomer or the combined weight of the monomers in a mixture thereof. If desired, the novel peresters may be combined with other known peroxides used for the polymerization or copolymerization of vinyl chloride, such as, for example, peroxydicarbonates, e.g. dicyclohexyl peroxydicarbonate, bis(4-tert.butyl-cyclohexyl)-peroxydicarbonate, bis(2-ethylhexyl)peroxydicarbonate, di-n-butyl peroxydicarbonate, di-sec.butyl peroxydicarbonate, diisopropyl peroxydicarbonate, dicetyl peroxydicarbonate and distearyl peroxydicarbonate; peresters, e.g. tert.butyl peroxypivalate, tert.butyl peroxy neodecanoate and tert.butyl peroxy-α-methyl-α-ethyl caproate; diacyl peroxides, e.g. dilauryl peroxide, didecanoyl peroxide, bis(3,5,5-trimethylhexanoyl)-peroxide, di-oxtanoyl peroxide, dinanoyl peroxide and the like.

These known peroxides can be incorporated in the vinyl chloride or in a mixture thereof with copolymerizable monomers in any suitable amount, preferably from 0.01 to 1.0% by weight, calculated on the monomer or the mixture of monomers.

It should be added that in the Netherlands Patent Application No. 6,503,292 laid open to public inspection there is described a perester derived from tert.butyl hydroperoxide and phenoxy acetic acid. This perester, however, has a lower reactivity than the novel peresters provided by this invention. The perester known from the Netherlands Patent Specification 6,503,292 is therefore less suitable to be used as such as an initiator in the mass or the suspension polymerization of vinyl chloride at a temperature in the range of 30° to 60° C.

An indication of the reactivity of peroxides at a certain temperature may be derived from the polymerization constant ($K_p$) of the formula $$R_o = \kappa_p [M] [I]^{1/2}$$

where
 $R_p$ = polymerization rate
 $K_p$ = polymerization rate constant
 $M$ = concentration of the monomer, and
 $I$ = initiator concentration The novel peresters provided by the invention also may be used as initiators for the polymerization or copolymerization of ethylenically unsaturated compounds other than vinyl chloride, viz. for the copolymerization of unsaturated polyester resins or the polymerization or copolymerization of other unsaturated compounds such as the ethylenically unsaturated monomers listed hereinbefore as examples of compounds polymerizable or copolymerizable with organic peroxides.

The term "unsaturated polyester resins" is used to identify mixtures of unsaturated polyesters and one or more monomers which contain one or more $CH_2=C<$ groups, such as e.g. styrene, vinyl toluene, methyl methacrylate, diallyl phthalate and divinyl benzene. The ratio of monomer to unsaturated polyester in the unsaturated polyester resin is generally 30–50% by weight of monomer to 70–50% by weight of polyester.

The unsaturated polyester may be obtained by reaction of approximately equivalent amounts of a polyhydric alcohol such as ethylene glycol, propylene glycol, diethylene glycol and an unsaturated dibasic carboxylic acid such as maleic acid, fumaric acid, itaconic acid or the related anhydrides in the presence, if desired, of a saturated polycarboxylic acid such as phthalic acid, isophthalic acid, tetrachlorophthalic acid, malonic acid, adipinic acid, succinic acid, sebacic acid and the like.

The novel peresters according to the invention may be obtained by reacting an acid halide, preferably an acid chloride having the general formula

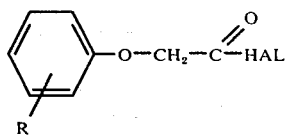

where R, represents hydrogen or a lower alkyl group or alkoxy group and HAL is a halogen such as chlorine or bromine, with 2,4,4-trimethyl pentyl-2-hydroperoxide. This reaction is preferably carried out in an organic solvent for the reactants such as, for example, diethyl ether, benzene, toluene or the like in the presence of an alkaline compound at a temperature below the decomposition temperature of the peroxide to be prepared. Diethyl ether is preferred as the solvent. Preferably, the alkaline compound is one which is soluble in the organic solvent such as, for example, an amine or ammonia.

After the reaction the peroxide obtained is isolated by filtration or by distilling off the solvent, after which the resulting peroxide is washed and dried in the usual manner and, if desired, recrystallized. The acid chloride required for the preparation may be obtained by bringing a phenol having the general formula

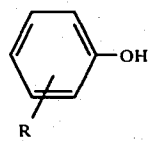

where R represents hydrogen, an alkyl group or alkoxy group with 1–6 C atoms, into reaction with monochloroacetic acid or a derivative thereof, followed by converting the resulting carboxylic acid into the corresponding acid chloride with the aid of a suitable chlorinating agent such as thionyl chloride or phosphorpentachloride.

The novel peresters according to the invention are safer than acetylcyclo hexanesulphonyl peroxide. This is shown by the results of the pressure vessel test.

In this test use is made of a 235-ml cylindrical steel vessel which is closed at its top with a latten breaking plate resistant to a pressure of 5.6–6.0 atmosphere and has in its side wall and exchangeable disk provided with an opening. The diameter of the opening in this disk increases from 1–24 mm. Upon quickly heating a sample in the pressure vessel the plate will burst or remain intact depending on the force developed as a result of the decomposition of the sample and the rate at which gas is discharged through the opening in the disk. The diameter of the opening in the disk which serves to prevent the plate from breaking is a measure of the safety of the sample. In a pressure vessel test carried out with 10 g of a 50% - solution of 2,4,4-trimethyl- pentyl-2-peroxyphenoxyacetate in toluene a maximum diameter of 10 mm was obtained. In a corresponding test with acetylcyclohexane sulphonyl peroxide a maximum diameter of 11.0 was measured. The solubility of the novel peresters provided by the invention in softeners such as dimethylphthalate which may be used as a phlegmatizing agent is higher than that of acetylcyclohexane sulphonyl peroxide.

For instance, whereas the solubility of acetylcyclohexane sulphonyl peroxide in dimethyl phthalate at −15° C. is 28%, that of 2,4,4-trimethylpentyl-2-peroxy phenoxyacetate in the same solvent at −30° C. is higher than 50%.

In order that the invention may be readily understood the following Examples are given by way of illustration only:

EXAMPLE I

To a mixture of 32.1 g (0.22 moles) of 2,4,4-trimethylpentyl-2-hydroperoxide and 150 ml of diethyl ether were added at −10° C. 17.4 g (0.22 moles) of pyridine and, subsequently, over a period of 45 minutes and also at −10° C, a mixture of 34.0 g (0.2 moles) of phenoxyacetyl chloride in 50 ml of diethyl ether. The reaction mixture was stirred for 2 hours at −10° C., followed by adding ice water to it and separating the organic superimposed layer. The same was successively washed with dilute acid, a bicarbonate solution and water, followed by reducing non-converted hydroperoxide with an aqueous solution of $Na_2SO_3$ and $Na_2S_2O_5$ at 0° C. After washing with water and drying over $MgSO_4$:1 $H_2O$, 45 g of dimethyl phthalate were added to the organic layer. Subsequently, the diethyl ether was distilled off at a temperature of 0° C. and a pressure of 5 mm Hg. There were obtained 97 g of a solution of 2,4,4-trimethylpentyl-2-peroxy-phenoxy acetate in dimethyl phthalate with a perester content of 54.7% (yield 95%) and a hydroperoxide content of less than 0.1%. By the same process but without the addition of dimethyl phthalate, 2,4,4-trimethylpentyl-2-peroxy-4-methyl phenoxyacetate, 2,4,4-trimethylpentyl-2-peroxy-4-tert. butyl phenoxyacetate and 2,4,4-trimethylpentyl-2-peroxy-4-methoxy phenoxyacetate with perester contents of 91.9, 81 and 87.2%, respectively, and in yields of 87.6, 58 and 64.3%, respectively were prepared from the appropriate acid chloride and 2,4,4-trimethylpentyl-2-hydroperoxide.

All peresters prepared showed an absorbance in the I.R. spectrum at 1765 $cm^{-1}$, which absorbance is attributable to the perester carbonyl group.

EXAMPLE II

A solution of 0.1 g of 2,4,4-trimethyl pentyl-2-peroxy phenoxyacetate in 50 g of pure methylmethacrylate was brought into a dilatometer which was subsequently evacuated of air. Then the dilatometer was placed in a thermostatically controlled bath whose temperature was the same as the polymerization temperature. Next, the variation with time of the contraction as a result of polymerization was measured for 1 hour. From the data obtained the $K_p$ value was calculated. Likewise, the $K_p$ values were calculated of other peroxides to be used according to the invention and, for comparison, of some known peroxides. The calculated $K_p$ values are shown in the following Table:

Table A

| peroxide | $K_p \times 10^4$ at 40° C. |
|---|---|
| 2,4,4-trimethyl pentyl-2-peroxy phenoxyacetate | 5.1 |
| 2,4,4-trimethyl pentyl-2-peroxy 4-methyl phenoxyacetate | 6.0 |
| 2,4,4-trimethyl pentyl-2-peroxy 4-methoxy phenoxyacetate | 7.8 |
| 2,4,4-trimethyl pentyl-2-peroxy 4-tert.butyl phenoxyacetate | 4.9 |
| acetylcyclohexane sulphonyl peroxides | 4.8 |
| tert.butyl peroxy phenoxyacetate | 2.9 |

EXAMPLE III

Into a 200-ml autoclave were charged 30 g of vinyl chloride, 60 ml of a 0.1%-solution of polyvinyl alcohol (Elvanol 50–42) in demineralized water and the various amounts of peroxides given in the following Table B. These amounts had been so chosen that taking into account the $K_p$ value and the molecular weight of the peroxide in accordance with the formula $$R_p = K_p [M] [I]^{1/2}$$

identical conversions could be expected.

The contents of the autoclave were subsequently heated to a temperature of 45° C. AFter 7 hours the polymerization reaction was stopped and the conversion was determined. The used peroxides and the results are shown in the following Table:

Table B

| peroxide | amount of peroxide | conversion |
|---|---|---|
| 2,4,4-trimethyl pentyl-2-peroxy phenoxyacetate | 0.057% | 82% |
| acetylcyclohexane sulphonyl peroxide | 0.050% | 80% |

Likewise, polymerization was carried out using the peroxides mentioned in Table C. Here, however, in both cases 0.061 millimoles of peroxide were added.

The results obtained are shown in the following Table:

Table C

| peroxide | conversion |
|---|---|
| 2,4,4-trimethylpentyl-2-peroxy phenoxyacetate | 81% |
| tert.butyl peroxy phenoxyacetate | 46% |

EXAMPLE IV

Into a 1-liter-autoclave there were charged 200 g of vinyl chloride, 400 ml of a 0.1%-solution of polyvinyl alcohol (Elavanol 50 – 42) in demineralized water and the amount of peroxide mentioned in Table D.

Subsequently, the contents of the autoclave were heated to temperature of 45° C. After 7 hours the polymerization reaction was stopped and the non-polymerized part of the vinyl chloride was discharged.

The polyvinyl chloride formed was removed by suction and dried for 12 hours at 50° C.

70 g of the resulting polyvinyl chloride were mixed with 30 g of dioctyl phthalate, 0.3 g of stearic acid, 1.0 g of tin-maleate-laurate and 0.5 g of carbon black and subsequently calendered for 4 minutes at 160° C.

Of the resulting sheet material the number of fisheyes per dm² was counted twice. The thermal stability of the sheet was measured three times at 130° C. in accordance with the Congo-red method (DIN-53381) with the time it took for the color to change to Congo-red being measured.

The numbers of fisheyes counted and the stabilities measured are given in the following Table:

Table D

| peroxide | amount of peroxide | number of fisheyes per dm² | | stability test change of color after ... sec. | |
|---|---|---|---|---|---|
| 2,4,4-trimethyl pentyl-2 peroxy phenoxyacetate | 114 mg | 2 | 6 | 202 206 | 208 |
| acetyl cyclohexane sulphonyl peroxide | 100 mg | 165 | 175 | 87 82 | 80 |

EXAMPLE V

Into a 200-ml autoclave there were charged 30 g of vinyl chloride, 60 ml of a 0.1%-solution of polyvinyl alcohol (Elvanol 50 – 42) in demineralized water and one of the peroxide combinations mentioned in Table E in the amount given therein.

The contents of the autoclave were then heated to the temperature mentioned in Table E. After polymerization the conversion was determined. The measured conversion are listed in Table E.

TABLE E

| amount of peroxide | amount of peroxide | polymerization temperature | polymerization time | conversion |
|---|---|---|---|---|
| (1) 0.022% | (2) 0.050% | 55° C. | 8 hours | 80% |
| (1) 0.022% | (2) 0.1% | 50° C. | 12 hours | 84% |
| (1) 0.022% | (2) 0.05% | 55° C. | 8 hours | 81% |

(1) 2,4,4-trimethyl pentyl-2-peroxy phenoxyacetate
(2) bis(4-tert.butylcyclohexyl) peroxy dicarbonate
(3) dilaurayl peroxide
(4) tert.butyl peroxypivalate

EXAMPLE VI

A "standard" resin for general purposes was prepared by reacting in a known way 1 mole of phthalic anhydride and 1 mole of maleic anhydride with 2.1 moles of propylene glycol to an acid number of 35, after which for each 66 parts by weight of the resulting unsaturated polyester there were added, with vigorous stirring, 33 parts by weight of styrene containing 0.01% hydroquinone and 0.005% p-tert.butyl catechol.

To the unsaturated polyester resin there was added such an amount of peroxide according to the invention that the mixture contained 1% by weight of pure peroxide. Of this mixture the following characteristics were determined in the way described in "Handbook of Reinforced Plastics of the S.P.J." ed. 1964, p. 51 ff.

The gel time was determined by placing a test tube containing 25 g of mixture in a thermostatically controlled bath of 40° C. By gel time is to be understood the time it takes for a sample to heat up from 23.3° C. to 45.6° C.

By min-cure time is to be understood the time it takes for a sample placed in a thermostatically controlled bath of 40° C. to heat up from 23.3° C. to peak temperature.

The critical temperature is the temperature of a thermostatically controlled bath in which the temperature of 25 g of sample contained in a test tube increases by at least 100° C. within 1 hour.

The used peroxides and the measured times and temperatures are listed in the following Table:

Table F

| peroxide | gel time | min-cure time | peak exoth. | critical temp. |
|---|---|---|---|---|
| 2,4,4-trimethyl-pentyl-2-peroxy phenoxyacetate | 7.4 min. | 8.3 min. | 217° C. | 30° C. |
| 2,4,4-trimethyl-pentyl-2-peroxy-4-methyl phenoxy- | | | | |

Table F-continued

| peroxide | gel time | min-cure time | peak exoth. | critical temp. |
|---|---|---|---|---|
| acetate | 8.2 min. | 9.1 min. | 214° C. | 30° C. |

Although the invention is described in detail for the purpose of illustration it is to be understood that such detail is solely for that purpose and that variations can be made therein by those skilled in the art without departing from the spirit and scope of the invention as it may be limited by the claims. What is claimed is:

1. Peresters having the general formula:

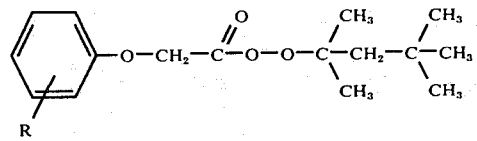

where R represents hydrogen or an alkyl group or an alkoxy group having 1–6 C-atoms.

2. The perester of claim 1 wherein R is an alkyl group having 1 to 6 carbon atoms.

3. The perester of claim 1 wherein R is an alkoxy group having 1 to 6 carbon atoms.

4. The perester of claim 1 wherein R is hydrogen.

* * * * *